United States Patent
Ferrari et al.

(10) Patent No.: US 11,666,746 B2
(45) Date of Patent: Jun. 6, 2023

(54) MEDICAL PRODUCT COMPRISING A FUNCTIONAL ELEMENT FOR THE INVASIVE USE IN A PATIENT'S BODY

(71) Applicant: ECP ENTWICKLUNGSGESELLSCHAFT MBH, Aachen (DE)

(72) Inventors: Marcus Ferrari, Wiesbaden (DE); Joerg Schumacher, Aachen (DE)

(73) Assignee: ECP ENTWICKLUNGSGESELLSCHAFT MBH, Aachen (DE)

( * ) Notice: Subject to any disclaimer, the term of this patent is extended or adjusted under 35 U.S.C. 154(b) by 327 days.

(21) Appl. No.: 16/718,431

(22) Filed: Dec. 18, 2019

(65) Prior Publication Data

US 2020/0268953 A1    Aug. 27, 2020

Related U.S. Application Data (63) Continuation of application No. 13/261,824, filed as application No. PCT/EP2012/067218 on Sep. 4, 2012, now Pat. No. 10,561,773.

(Continued)

(30) Foreign Application Priority Data

Sep. 5, 2011    (EP) .................................. 11075206

(51) Int. Cl.
*A61M 60/139*    (2021.01)
*A61M 60/148*    (2021.01)
(Continued)

(52) U.S. Cl.
CPC ............. *A61M 60/148* (2021.01); *A61B 5/06* (2013.01); *A61B 5/318* (2021.01); *A61M 60/139* (2021.01);
(Continued)

(58) Field of Classification Search
CPC ......... A61B 5/06; A61B 5/0402; A61M 1/122
See application file for complete search history.

(56) References Cited

U.S. PATENT DOCUMENTS

| | | | |
|---|---|---|---|
| 3,510,229 | A | 5/1970 | Smith |
| 3,568,659 | A | 3/1971 | Karnegis |

(Continued)

FOREIGN PATENT DOCUMENTS

| | | | |
|---|---|---|---|
| CA | 1008330 | A | 4/1977 |
| CA | 2311977 | A1 | 12/2000 |

(Continued)

OTHER PUBLICATIONS

Third Office Action issued in corresponding Chinese Patent Application No. 201711426842.3 dated Jul. 5, 2021, 9 pp.

(Continued)

*Primary Examiner* — Rex R Holmes
*Assistant Examiner* — Jennifer L Ghand
(74) *Attorney, Agent, or Firm* — Botos Churchill IP Law LLP (57) ABSTRACT

So as to be able to determine the position of a functional element as precisely as possible during the invasive use of a blood pump in a patient's body without the use of imaging methods, the blood pump is connected to a main sensor which records signals of the patient's heart, which are compared to other electrophysiological heart signals recorded by several sensors distributed on the body surface so as to allow the position of the blood pump to be determined by way of linking.

24 Claims, 6 Drawing Sheets

Related U.S. Application Data (60) Provisional application No. 61/531,030, filed on Sep. 5, 2011.

(51) Int. Cl.

| | | |
|---|---|---|
| *A61B 5/06* | (2006.01) | |
| *A61B 5/318* | (2021.01) | |
| *A61M 60/268* | (2021.01) | |
| *A61M 60/554* | (2021.01) | |
| *A61M 60/462* | (2021.01) | |
| *A61M 60/531* | (2021.01) | |
| A61F 2/82 | (2013.01) | |
| A61M 60/113 | (2021.01) | |
| A61M 60/414 | (2021.01) | |

(52) U.S. Cl.
CPC ........ *A61M 60/268* (2021.01); *A61M 60/462* (2021.01); *A61M 60/531* (2021.01); *A61M 60/554* (2021.01); A61F 2/82 (2013.01); A61F 2250/0096 (2013.01); A61M 60/113 (2021.01); A61M 60/414 (2021.01); A61M 2205/32 (2013.01)

(56) References Cited

U.S. PATENT DOCUMENTS

| | | |
|---|---|---|
| 3,802,551 A | 4/1974 | Somers |
| 3,812,812 A | 5/1974 | Hurwitz |
| 4,014,317 A | 3/1977 | Bruno |
| 4,207,028 A | 6/1980 | Ridder |
| 4,559,951 A | 12/1985 | Dahl et al. |
| 4,563,181 A | 1/1986 | Wijayarathna et al. |
| 4,679,558 A | 7/1987 | Kensey et al. |
| 4,686,982 A | 8/1987 | Nash |
| 4,747,821 A | 5/1988 | Kensey et al. |
| 4,749,376 A | 6/1988 | Kensey et al. |
| 4,753,221 A | 6/1988 | Kensey et al. |
| 4,801,243 A | 1/1989 | Norton |
| 4,817,613 A | 4/1989 | Jaraczewski et al. |
| 4,919,647 A | 4/1990 | Nash |
| 4,957,504 A | 9/1990 | Chardack |
| 4,969,865 A | 11/1990 | Hwang et al. |
| 4,995,857 A | 2/1991 | Arnold |
| 5,011,469 A | 4/1991 | Buckberg et al. |
| 5,040,944 A | 8/1991 | Cook |
| 5,042,984 A | 8/1991 | Kensey et al. |
| 5,052,404 A | 10/1991 | Hodgson |
| 5,061,256 A | 10/1991 | Wampler |
| 5,092,844 A | 3/1992 | Schwartz et al. |
| 5,097,849 A | 3/1992 | Kensey et al. |
| 5,108,411 A | 4/1992 | Mckenzie |
| 5,112,292 A | 5/1992 | Hwang et al. |
| 5,113,872 A | 5/1992 | Jahrmarkt et al. |
| 5,117,838 A | 6/1992 | Palmer et al. |
| 5,118,264 A | 6/1992 | Smith |
| 5,145,333 A | 9/1992 | Smith |
| 5,163,910 A | 11/1992 | Schwartz et al. |
| 5,169,378 A | 12/1992 | Figuera |
| 5,183,384 A | 2/1993 | Trumbly |
| 5,191,888 A | 3/1993 | Palmer et al. |
| 5,201,679 A | 4/1993 | Velte et al. |
| 5,275,580 A | 1/1994 | Yamazaki |
| 5,373,619 A | 12/1994 | Fleischhacker et al. |
| 5,376,114 A | 12/1994 | Jarvik |
| 5,391,199 A | 2/1995 | Ben-haim |
| 5,443,489 A | 8/1995 | Ben-haim |
| 5,480,422 A | 1/1996 | Ben-haim |
| 5,501,574 A | 3/1996 | Raible |
| 5,531,789 A | 7/1996 | Yamazaki et al. |
| 5,546,951 A | 8/1996 | Ben-haim |
| 5,568,809 A | 10/1996 | Ben-haim |
| 5,694,945 A | 12/1997 | Ben-haim |
| 5,697,377 A | 12/1997 | Wittkampf |
| 5,701,911 A | 12/1997 | Sasamine et al. |
| 5,713,946 A | 2/1998 | Ben-haim |
| 5,755,784 A | 5/1998 | Jarvik |
| 5,776,190 A | 7/1998 | Jarvik |
| 5,813,405 A | 9/1998 | Montano et al. |
| 5,820,571 A | 10/1998 | Erades et al. |
| 5,840,025 A | 11/1998 | Ben-haim |
| 5,851,174 A | 12/1998 | Jarvik et al. |
| 5,882,329 A | 3/1999 | Patterson et al. |
| 5,888,241 A | 3/1999 | Jarvik |
| 5,938,672 A | 8/1999 | Nash |
| 5,983,126 A | 11/1999 | Wittkampf |
| 6,030,397 A | 2/2000 | Monetti et al. |
| 6,129,704 A | 10/2000 | Forman et al. |
| 6,152,693 A | 11/2000 | Olsen et al. |
| 6,168,624 B1 | 1/2001 | Sudai |
| 6,226,546 B1 | 5/2001 | Evans |
| 6,254,359 B1 | 7/2001 | Aber |
| 6,302,910 B1 | 10/2001 | Yamazaki et al. |
| 6,308,632 B1 | 10/2001 | Shaffer |
| 6,336,939 B1 | 1/2002 | Yamazaki et al. |
| 6,346,120 B1 | 2/2002 | Yamazaki et al. |
| 6,387,125 B1 | 5/2002 | Yamazaki et al. |
| 6,503,224 B1 | 1/2003 | Forman et al. |
| 6,506,025 B1 | 1/2003 | Gharib |
| 6,508,787 B2 | 1/2003 | Erbel et al. |
| 6,517,315 B2 | 2/2003 | Belady |
| 6,527,521 B2 | 3/2003 | Noda |
| 6,533,716 B1 | 3/2003 | Schmitz-rode et al. |
| 6,537,030 B1 | 3/2003 | Garrison |
| 6,537,315 B2 | 3/2003 | Yamazaki et al. |
| 6,592,612 B1 | 7/2003 | Samson et al. |
| 6,652,548 B2 | 11/2003 | Evans et al. |
| 6,719,791 B1 | 4/2004 | Nuesser et al. |
| 6,860,713 B2 | 3/2005 | Hoover |
| 6,892,091 B1 | 5/2005 | Ben-haim et al. |
| 6,945,977 B2 | 9/2005 | Demarais et al. |
| 6,981,942 B2 | 1/2006 | Khaw et al. |
| 7,022,100 B1 | 4/2006 | Aboul-hosn et al. |
| 7,027,875 B2 | 4/2006 | Siess et al. |
| 7,074,018 B2 | 7/2006 | Chang |
| 7,179,273 B1 | 2/2007 | Palmer et al. |
| 7,393,181 B2 | 7/2008 | Mcbride et al. |
| 7,467,929 B2 | 12/2008 | Nuesser et al. |
| 7,731,675 B2 | 6/2010 | Aboul-hosn et al. |
| 7,927,068 B2 | 4/2011 | Mcbride et al. |
| 7,934,909 B2 | 5/2011 | Nuesser et al. |
| 8,388,541 B2 | 3/2013 | Messerly et al. |
| 8,388,546 B2 | 3/2013 | Rothenberg |
| 10,561,773 B2* | 2/2020 | Ferrari ................ A61M 60/148 |
| 2001/0018569 A1 | 8/2001 | Erbel et al. |
| 2001/0021831 A1 | 9/2001 | Fleischhacker et al. |
| 2002/0123661 A1 | 9/2002 | Verkerke et al. |
| 2003/0135086 A1 | 7/2003 | Khaw et al. |
| 2003/0231959 A1 | 12/2003 | Snider |
| 2004/0044266 A1 | 3/2004 | Siess et al. |
| 2004/0046466 A1 | 3/2004 | Siess et al. |
| 2004/0093074 A1 | 5/2004 | Hildebrand et al. |
| 2004/0215222 A1 | 10/2004 | Krivoruchko |
| 2004/0215228 A1 | 10/2004 | Simpson et al. |
| 2006/0008349 A1 | 1/2006 | Khaw |
| 2006/0062672 A1 | 3/2006 | Mcbride et al. |
| 2006/0195004 A1 | 8/2006 | Jarvik |
| 2008/0132747 A1 | 6/2008 | Shifflette |
| 2008/0262584 A1 | 10/2008 | Bottomley et al. |
| 2008/0306327 A1 | 12/2008 | Shifflette |
| 2009/0060743 A1 | 3/2009 | Mcbride et al. |
| 2009/0093764 A1 | 4/2009 | Pfeffer et al. |
| 2009/0093796 A1 | 4/2009 | Pfeffer et al. |
| 2009/0234328 A1 | 9/2009 | Cox et al. |
| 2009/0259124 A1 | 10/2009 | Rothenberg |
| 2010/0036227 A1 | 2/2010 | Cox et al. |
| 2010/0041939 A1 | 2/2010 | Siess |
| 2010/0240944 A1 | 9/2010 | Maschke |
| 2010/0268017 A1 | 10/2010 | Siess |
| 2010/0317981 A1 | 12/2010 | Grunwald |
| 2010/0318026 A1 | 12/2010 | Grunwald |
| 2011/0015533 A1 | 1/2011 | Cox et al. |
| 2011/0196248 A1 | 8/2011 | Grunwald |
| 2011/0238172 A1 | 9/2011 | Akdis |

(56) References Cited

U.S. PATENT DOCUMENTS

| | | |
|---|---|---|
| 2011/0275884 A1 | 11/2011 | Scheckel |
| 2012/0039711 A1 | 2/2012 | Roehn |
| 2012/0041254 A1 | 2/2012 | Scheckel |
| 2012/0046648 A1 | 2/2012 | Scheckel |
| 2012/0093628 A1 | 4/2012 | Liebing |
| 2012/0101455 A1 | 4/2012 | Liebing |
| 2012/0142994 A1 | 6/2012 | Toellner |
| 2012/0184803 A1 | 7/2012 | Simon et al. |
| 2012/0224970 A1 | 9/2012 | Schumacher et al. |
| 2012/0234411 A1 | 9/2012 | Scheckel |
| 2012/0237353 A1 | 9/2012 | Schumacher et al. |
| 2012/0237357 A1 | 9/2012 | Schumacher et al. |
| 2012/0264523 A1 | 10/2012 | Liebing |
| 2012/0265002 A1 | 10/2012 | Roehn et al. |
| 2012/0294727 A1 | 11/2012 | Roehn |
| 2012/0301318 A1 | 11/2012 | Er |
| 2012/0308406 A1 | 12/2012 | Schumacher |
| 2013/0019968 A1 | 1/2013 | Liebing |
| 2013/0041202 A1 | 2/2013 | Toellner |
| 2013/0060077 A1 | 3/2013 | Liebing |
| 2013/0066139 A1 | 3/2013 | Wiessler et al. |
| 2013/0085318 A1 | 4/2013 | Toellner |
| 2013/0093058 A1 | 4/2013 | Nakai |
| 2013/0123597 A1 | 5/2013 | Rothenberg |
| 2013/0177409 A1 | 7/2013 | Schumacher et al. |
| 2013/0177432 A1 | 7/2013 | Toellner et al. |
| 2013/0204362 A1 | 8/2013 | Toellner et al. |
| 2013/0237744 A1 | 9/2013 | Pfeffer et al. |
| 2013/0251502 A1 | 9/2013 | Ketcham et al. |
| 2014/0039465 A1 | 2/2014 | Schulz et al. |
| 2014/0067056 A1 | 3/2014 | Schimpf et al. |
| 2014/0255176 A1 | 9/2014 | Bredenbreuker et al. |
| 2014/0303596 A1 | 10/2014 | Schumacher et al. |
| 2019/0184079 A1* | 6/2019 | Yu ........................ A61M 60/422 |

FOREIGN PATENT DOCUMENTS

| | | |
|---|---|---|
| CA | 2701809 A1 | 4/2009 |
| CA | 2701810 A1 | 4/2009 |
| DE | 2207296 A1 | 8/1972 |
| DE | 2113986 A1 | 9/1972 |
| DE | 2233293 A1 | 1/1973 |
| DE | 2613696 A1 | 10/1977 |
| DE | 4124299 A1 | 1/1992 |
| DE | 69103295 T2 | 12/1994 |
| DE | 19535781 A1 | 3/1997 |
| DE | 19711935 A1 | 4/1998 |
| DE | 29804046 U1 | 4/1998 |
| DE | 69407869 T2 | 4/1998 |
| DE | 69017784 T3 | 4/2000 |
| DE | 69427390 T2 | 9/2001 |
| DE | 10059714 C1 | 5/2002 |
| DE | 10108810 A1 | 8/2002 |
| DE | 10155011 A1 | 5/2003 |
| DE | 69431204 T2 | 8/2003 |
| DE | 10336902 B3 | 8/2004 |
| DE | 102010011998 A1 | 9/2010 |
| EP | 0410602 A1 | 1/1991 |
| EP | 0480102 A1 | 4/1992 |
| EP | 480102 A1 | 4/1992 |
| EP | 0560000 A2 | 9/1993 |
| EP | 560000 A2 | 9/1993 |
| EP | 0659443 A1 | 6/1995 |
| EP | 0629412 B1 | 1/1998 |
| EP | 0884064 A2 | 12/1998 |
| EP | 884064 A2 | 12/1998 |
| EP | 0916359 A1 | 5/1999 |
| EP | 1066851 A1 | 1/2001 |
| EP | 0914171 B1 | 10/2001 |
| EP | 0768091 B1 | 7/2003 |
| EP | 0916359 B1 | 9/2004 |
| EP | 0951302 B1 | 9/2004 |
| EP | 1114648 B1 | 9/2005 |
| EP | 1019117 B1 | 11/2006 |
| EP | 1337288 B1 | 3/2008 |
| EP | 2218469 A1 | 8/2010 |
| EP | 2229965 A1 | 9/2010 |
| EP | 2301598 A1 | 3/2011 |
| EP | 2308524 A1 | 4/2011 |
| EP | 2343091 A1 | 7/2011 |
| EP | 2345440 A1 | 7/2011 |
| EP | 2366412 A2 | 9/2011 |
| EP | 1651290 B1 | 1/2012 |
| EP | 2497521 A1 | 9/2012 |
| EP | 2606919 A1 | 6/2013 |
| EP | 2606920 A1 | 6/2013 |
| EP | 2607712 A1 | 6/2013 |
| GB | 1370546 A | 10/1974 |
| GB | 2239675 A | 7/1991 |
| RU | 2229899 C2 | 6/2004 |
| WO | 9202263 A1 | 2/1992 |
| WO | 9302732 A1 | 2/1993 |
| WO | 9303786 A1 | 3/1993 |
| WO | 9314805 A1 | 8/1993 |
| WO | 94001148 A1 | 1/1994 |
| WO | 9405347 A1 | 3/1994 |
| WO | 9409835 A1 | 5/1994 |
| WO | 9420165 A2 | 9/1994 |
| WO | 9420165 A3 | 9/1994 |
| WO | 9500186 A1 | 1/1995 |
| WO | 9523000 A2 | 8/1995 |
| WO | 9618358 A1 | 6/1996 |
| WO | 9625969 A2 | 8/1996 |
| WO | 9744071 A1 | 11/1997 |
| WO | 9853864 A1 | 12/1998 |
| WO | 9919017 A1 | 4/1999 |
| WO | 0027446 A1 | 5/2000 |
| WO | 0043054 A2 | 7/2000 |
| WO | 0062842 A1 | 10/2000 |
| WO | 2001007760 A1 | 2/2001 |
| WO | 2001007787 A1 | 2/2001 |
| WO | 2001083016 A2 | 11/2001 |
| WO | 2003057013 A2 | 7/2003 |
| WO | 2003103745 A2 | 12/2003 |
| WO | 2005002646 A1 | 1/2005 |
| WO | 2005016416 A1 | 2/2005 |
| WO | 2005021078 A1 | 3/2005 |
| WO | 2005030316 A1 | 4/2005 |
| WO | 2005032620 A1 | 4/2005 |
| WO | 2005081681 A2 | 9/2005 |
| WO | 2006020942 A1 | 2/2006 |
| WO | 2006034158 A2 | 3/2006 |
| WO | 2006133209 A1 | 12/2006 |
| WO | 2007003351 A1 | 1/2007 |
| WO | 2007103390 A2 | 9/2007 |
| WO | 2007103464 A2 | 9/2007 |
| WO | 2007112033 A2 | 10/2007 |
| WO | 2008017289 A2 | 2/2008 |
| WO | 2008034068 A2 | 3/2008 |
| WO | 2008054699 A2 | 5/2008 |
| WO | 2008106103 A2 | 9/2008 |
| WO | 2008116765 A2 | 10/2008 |
| WO | 2008124696 A1 | 10/2008 |
| WO | 2008137352 A1 | 11/2008 |
| WO | 2008137353 A1 | 11/2008 |
| WO | 2009015784 A1 | 2/2009 |
| WO | 2010133567 A1 | 11/2010 |
| WO | 2013034547 A1 | 3/2013 |
| WO | 2013092971 A1 | 6/2013 |
| WO | 2013093001 A2 | 6/2013 |
| WO | 2013093058 A1 | 6/2013 |

OTHER PUBLICATIONS

First Office Action issued in Chinese Patent Application No. 201711426842.3 dated Nov. 6, 2019.
Second Office Action issued in Chinese Patent Application No. 201711426842.3 dated Jun. 19, 2020.
English Language Translation of DE102010011998A1.
English Language Translation of EP2343091A1.

(56) References Cited

OTHER PUBLICATIONS

Search Report from European Patent Application No. 11075206, dated Mar. 6, 2012 (12 pages).

\* cited by examiner

MEDICAL PRODUCT COMPRISING A FUNCTIONAL ELEMENT FOR THE INVASIVE USE IN A PATIENT'S BODY

CROSS-REFERENCE TO RELATED APPLICATIONS

This application is a continuation of U.S. application Ser. No. 13/261,824, filed May 19, 2014, now U.S. Pat. No. 10,561,773, which is a national stage entry of PCT/EP2012/067218, filed Sep. 4, 2012, published as WO 2013/034547, which claims the benefit of U.S. Provisional Patent Application No. 61/531,030, filed Sep. 5, 2011, and European Patent Application No. 11075206.0, filed Sep. 5, 2011. The disclosures of each of the foregoing applications and patent are hereby incorporated by reference in their entirety.

The invention relates to the field of medical engineering, and more particularly to micromechanics and medical measuring technology.

BACKGROUND OF THE INVENTION

Modern medicine employs microinvasive techniques in a variety of ways and to an increasing degree, so as to achieve maximum supportive, therapeutic or diagnostic success with minimal impact on the patient.

Examples of such techniques include the insertion of stents in blood vessels, the use of thrombus filters, the removal of deposits in blood vessels by milling, and the support or temporary or partial replacement of a patient's cardiac function through micropumps/blood pumps that are introduced in blood vessels.

Many of these techniques require appropriate functional elements to be introduced via the bloodstream into the patient's body by means of a catheter and to be positioned within the bloodstream in the most expedient manner possible.

Precise position control to as great an extent as possible is not only desirable, initially or during acute use, for example on a milling head, as well as in the long term, but also decisive for the success of the invasive measure.

Positioning plays a critical role especially with blood pumps because these often remain in the patient's body for extended periods and must operate reliably without constant supervision by medical staff, wherein in the case of a catheter configuration, notably with access via a femoral artery, the risk of shifting exists due to active or passive body movements. The precision with which blood pumps are placed is also subject to stringent requirements, especially when these are located in the vicinity of a heart valve or cooperate with a heart valve.

Often times the positions of the corresponding functional elements are analyzed using radioscopy or by means of transesophageal echocardiography. However, these methods are tied to complex devices, which are not always available. This makes the position determination not only complex and expensive, but in many instances it is also not practical or useful given the extreme time pressure. While in emergencies, it is possible to place an intra-aortic pump blindly by measuring the distance between the puncture site in the groin and the jugular notch. However, this presupposes normal anatomic circumstances and carries with it the risk of misplacement in the contralateral femoral artery. This method is also imprecise because the individual anatomic features of the aorta are not predictable. If the functional element, in particular the pump, cannot be optimally placed, the supporting effect of such a pump is not optimal, and other functional elements can likewise not function optimally.

In addition to the pure transillumination method, other options are known from the prior art for determining the position of a component, and more particularly that of a cardiac catheter, substantially precisely.

U.S. Pat. No. 5,983,126, for example, discloses the application of three orthogonal external signals outside the patient body to the positioning area, wherein a probe is used to measure the influence of the three signals on the functional element and thus conclude the position. The corresponding external signals must be designed so that they do not interfere with the electrophysiological signals of the heart.

U.S. Pat. No. 6,226,546 B1 describes a catheter localization method using a plurality of acoustic probes at the catheter head, wherein signals emitted by the probes are received via acoustic receivers and processed by a processing unit so as to determine the position and map the anatomic environment of the probes.

A catheter localization method having an accuracy of approximately 1 mm is known from U.S. Pat. No. 5,391,199, in which a transmitter outside the patient body emits signals by means of an antenna and receiving antennas are provided at the catheter tip, which are connected to a receiver for processing the signals. The signals are compared to corresponding reference signals from reference antennas in the patient's body.

Devices and methods for recording and mapping the electrophysiological activity inside a heart by means of a cardiac catheter are known from U.S. Pat. No. 6,892,091 B1. The corresponding catheter also comprises a position sensor, which is designed as an electromagnetic sensor. The exemplary embodiment regarding the use of such a position sensor described involves the application of magnetic fields which are generated outside the patient body and which act on the position sensor, so that both a position and an orientation of the sensor, and thus of the catheter, can be determined by means of the sensor. In addition, the comparison to reference signals of additionally introduced catheters is described.

The methods known from the prior art all have complex equipment in common, either in form of imaging devices or of additional signal sources outside the patient body. Such methods are not suitable for everyday use that is otherwise unproblematic, with a blood pump that is operated for cardiac support purposes for extended periods without the supervision of medical staff.

BRIEF SUMMARY OF THE INVENTION

It is the object of the present invention to create a medical product which allows simple and reliable position determination during the invasive use of blood pumps, having particularly low complexity in terms of the apparatus.

The object is achieved according to the invention by way of the characteristics of claim 1, 9 or 14.

The invention makes it possible to control the position of a blood pump for days, weeks and months, even when it is operated automatically, and even with customary patient movements.

In the variant of claim 1, a medical product comprises a functional element in form of a blood pump for the invasive use in a patient's body, having a main sensor, which has a fixed spatial relationship relative to the blood pump. The main sensor in particular has a fixed, known distance from the blood pump. In addition, a processing unit is provided, which receives signals from the main sensor representing the signals or readings acquired by the main sensor and which determines at least one variable representing the position of the blood pump from signals from the main sensor, on the basis of electrophysiological signals of the heart.

It has long been known to measure electrophysiological signals on a beating heart. A typical application is the conventional electrocardiogram using electrodes, which are placed on a patient's skin in a suitable number, depending on the type of lead and complexity.

The time-variable signals are typically processed to form a vector which represents a fingerprint characterizing the respective individual heart. Because the respective recorded electrophysiological signals are heavily dependent on the site of the lead, a comparison between a measured signal and a typical electrocardiogram of the same person allows a conclusion of the position of the measurement/lead. It also optionally possible to conclude the positions of individual measuring electrodes.

To this end, the invention comprises a corresponding processing unit which is either directly connected to electrodes or which can be supplied with appropriately preprocessed data from ECG electrodes.

If the signals recorded by the main sensor are continually or periodically compared or linked to the electrophysiological data of the heart, it is possible to monitor the position of the main sensor, and thus that of the functional element/the blood pump having a fixed spatial relationship therewith, on an ongoing basis. In a particularly simple design, the main sensor is, for example, disposed on the blood pump itself or at a fixed distance therefrom, for example at one of the ends of the pump, if the blood pump is designed as substantially elongate body.

The method may similarly be applied using impedance measurements, or the analysis of a pulse curve detected by the main sensor as compared to the corresponding readings from a peripheral artery (for example arm or leg artery). Here, the time delay between the pressure increase maxima and minima is measured and indicates changes of the position or of the circulatory characteristics.

In a particular design of the invention, the processing unit can be directly connected to auxiliary sensors which record appropriate electrophysiological heart signals, and the processing unit can further process the signals from the main sensor with currently detected signals from the auxiliary sensors, or with data determined therefrom, for example if the data has been preprocessed to obtain an ECG. The advantage of this procedure is, for example, that the temporal rhythm of the signals detected by the main sensor can be directly synchronized with the rhythm of the signals from the auxiliary sensors.

The signal obtained by way of the main sensor and the vector of the limb leads can, for example in relation to a specific limb lead in accordance with the technique described by Goldberger, can then be utilized to define an optimal position vector. This vector can be continuously compared to the ECG vector obtained by way of the main sensor, whereby the actual position of the main sensor, and hence the position of the functional element, can be determined for every beat of the heart and compared to a desired position. Data about measured vectors and data from the main sensor detected in this respect can be recorded for calibration purposes with various known positions of the main sensor and/or of the functional element/of the blood pump (for example with simultaneous use of an imaging method), and a kind of "map" of the position can thus be stored based on exemplary data and can later be compared to currently detected data. For example, it is possible to determine the data record that is closest to the currently detected data record, and the position data which is stored for this closest data record can be used to draw a conclusion of the current position of the main sensor and/or of the functional element.

It is also possible for the processing unit to be connected to a memory unit in which the previously detected electrophysiological heart signals, and more particularly those of the patient's heart, are stored, and for the processing unit to link signals from the main sensor to stored heart signals and/or to other previously detected data, or data determined therefrom, so as to determine the variable representing the position of the functional element.

Temporal scaling of the data currently obtained by means of the main sensor is then necessary, or at least advantageous, for the purpose of a comparison to the stored ECG data, before the currently obtained vector or the currently obtained data can be compared to the stored data.

It is also conceivable to establish a relationship between the stored reference ECG data and the currently obtained ECG data from the auxiliary sensors and to obtain data on this basis, to which the signals from the main sensor are compared.

The main sensor typically comprises an electrode and/or antenna for recording electrophysiological signals. In the patient's body, such signals propagate electrodynamically as well as galvanically, so that they can be recorded well even at a distance from the heart. The coupling of a corresponding electrode to a measuring circuit plays a decisive role in the frequency response that is attained and whether it is a measuring electrode or an antenna.

Advantageously, it is also possible to provide more than one electrode or antenna on the main sensor. For example, two mutually spaced electrodes/antennas can produce a more precise determination of the position and orientation. However, it is also conceivable to use more than two electrodes. It is then possible to obtain a multidimensional vector from the data detected by the main sensor.

The invention can be implemented particularly advantageously with a blood pump which can be moved through a blood vessel by means of a catheter. Information about blood pumps, which are typically used outside, or also inside, the heart and in which the distance from the ventricle inlet or outlet or the position along the blood vessel is crucial for successful use, can be of particular interest.

Typical functional elements according to the invention can be blood pumps, and more particularly intra-aortic balloon pumps or rotary pumps.

The positioning relative to the ventricle is especially important with blood pumps. An intra-aortic balloon pump, for example, must be positioned outside in front of the ventricle at a defined distance, while a rotary pump should protrude partially into the ventricle.

In this respect, according to the invention the variable representing the position of the functional element can be the distance of the functional element from the mouth of a blood vessel in which the functional element is located into a chamber of the heart, notably along the course of the blood vessel.

According to a particular design of the invention, it is also possible for the main sensor to comprise a sensor for detecting a fluid mechanics variable, in particular a pressure sensor or a sensor for the flow velocity of the blood, or it is possible for the main sensor to be such a sensor, and it is possible for the processing unit to detect the temporal relationship between currently detected electrophysiological heart signals and a measurand characterizing the blood flow at the position of the main sensor and to determine on this basis a variable representative of the position of the functional element. In this case, essentially the delay of flow modulations generated by the cardiac activity, and more particularly of the changes in the flow velocity or pressure changes in the blood circulation system, is used to determine the location of the main sensor or of the functional element formed by a blood pump. Because the electrophysiological signals are recorded virtually without delay, yet the migration of a pressure wave takes place considerably more slowly, the time delay of a pressure wave maximum, for example, can be used to calculate the distance of the main sensor from the heart when the migration velocity is known. Instead of the pressure wave maximum, it is also possible to use other typical points of the pressure curve in the vascular system.

Another advantageous embodiment of the invention relates to a medical product in which the processing unit detects changes in the variable representing the position of the functional element and generates a signal, especially an alarm signal, when a threshold for the change is exceeded. (In the context of this patent application, "exceed" is to be understood as any interesting deviation from a threshold, i.e. a deviation below and/or above a certain threshold.) When an alarm signal is emitted, the patient can then seek the care of medical staff, or an adjustment can be carried out independently and automatically by means of actuators.

Another advantageous embodiment of the invention relates to a medical product in which the processing unit comprises a memory unit for a determined position of the functional element, and a comparison unit which compares continuously determined position values of the functional element to a value stored in the memory unit, determines a difference value between the stored value and a currently determined position value, and emits a signal if the difference value exceeds an established threshold.

According to a further embodiment of the invention, the processing unit is advantageously connected to a unit which generates a signal representing the current power, and more particularly the rotational speed of the blood pump if it is a rotary pump, and the processing unit comprises a correction unit for taking the power of the blood pump into consideration in the determination of the position of the functional element.

In particular the rotational speed of a rotary pump can influence the cardiac function and thus influence the signals which are used for the position determination. The influence of the rotational speed can thus be advantageously determined, stored in characteristic fields and taken into consideration in the evaluation.

The invention further relates to a medical product, as was already partially described above by way of example, and to a method for operating a blood pump in the body of a patient, in particular in a blood vessel, characterized in that a variable representing the position of the blood pump is determined by a main sensor, which has a fixed spatial relationship relative to the pump, locally detecting at least one parameter which is defined by the cardiac function of the patient and by converting the parameter into signals, and by linking identical or additional data or signals which characterize the cardiac function and which are detected, for example in the same blood vessel in which the blood pump is located, in a known position which is spaced from the pump, to the signals from the main sensor.

The invention advantageously also refers to a method for operating a blood pump in which first the blood pump is positioned in the patient's body at a desired location using an imaging method, characterized in that thereafter, in accordance with the method of claim 14, a variable representing the position of the blood pump is determined and stored as a calibration variable, at a later time the method in accordance with claim 14 is carried out, and the determined variable representing the position of the blood pump is compared to the calibration variable, and a signal is emitted if a threshold value of the variance from the calibration value is exceeded.

The signal can be an optical and/or acoustic warning signal which is directed to the patient or medical staff, or it can be directly conducted to a device for adjusting the pump.

In an advantageous embodiment of the invention, the processing unit may be designed to process signals from an impedance sensor and/or from a blood pressure sensor and/or from a respiratory activity sensor and/or from a sensor for the oxygen content in the blood, and/or the processing unit may be connected to one or more sensors of the aforementioned sensor types. By linking one or more of the aforementioned measurands to detected signals or measurement results of the main sensor, it is thus possible to determine the position of the main sensor, either directly or by way of a comparison to stored reference data. The main sensor can likewise be suitable for detecting the aforementioned measurands, these being impedance, blood pressure, respiratory activity or oxygen content.

According to one embodiment of the invention, an auxiliary sensor, which like the main sensor comprises a variable characterizing the blood flood, and more particularly the variable measured also by the main sensor, is disposed in a position, in particular in a known position, which is spaced from the unknown position of the main sensor.

BRIEF DESCRIPTION OF THE DRAWINGS

The invention will be described hereafter in an exemplary embodiment and is shown in drawings.

In the drawings.

DETAILED DESCRIPTION OF THE INVENTION

Figure 1:
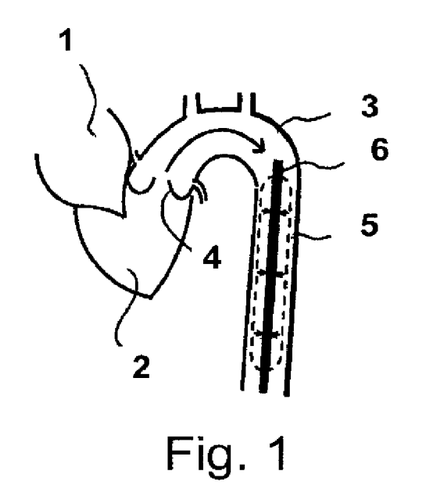
FIG. 1 is a schematic view of an intra-aortic balloon pump in a blood vessel close to the heart, wherein the balloon takes on the compressed from thereof.

FIG. 1 is a schematic view of a portion of a heart with a left atrium 1, a left ventricle 2, from which a blood vessel 3 extends, and heart valves 4, which allow the blood to flow from the left ventricle 2 into the blood vessel.

FIG. 1 shows the state in the systolic phase, in which the balloon pump 5 is present with the balloon being in the compressed state. In this case, the balloon pump 5 forms the functional element, which can be used to support the heart by relieving the left ventricle during acute cardiac insufficiency, coronary heart disease and similar instances. Such an intra-aortic balloon pump can be used both within the scope of coronary bypass surgeries when treating cardiogenic shock and acute myocardial infarction, and with acute myocarditis, cardiomyopathy and acute left heart failure. It is typically advanced into the aorta starting from the femoral artery and is then located with the tip of the pump catheter at the end of the aortic arch. The balloon can typically be filled with a volume of 40 ml helium gas over a length of 20 cm and thus be expanded. The balloon is periodically filled and emptied (compressed) by an external pneumatic system. Because the balloon filling and emptying take place counter to the cardiac activity, the afterload for the left ventricle is decreased during the systole, which results in an increased ejection fraction and decreased myocardial oxygen consumption.

Figure 2:
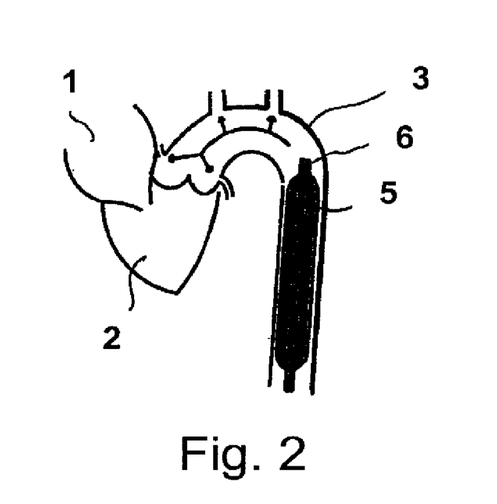
FIG. 2 shows the configuration of FIG. 1 with an expanded balloon.

The diastolic filling of the pump balloon, as shown in FIG. 2, displaces an average of 40 ml of blood, whereby the diastolic blood pressure is raised and the organ blood flow, and the coronary blood flow in particular, is improved during this phase.

The key in this connection is to position the functional element as optimally as possible in the aorta relative to the heart valve 4 or the mouth of the blood vessel into the left ventricle.

Figure 3:
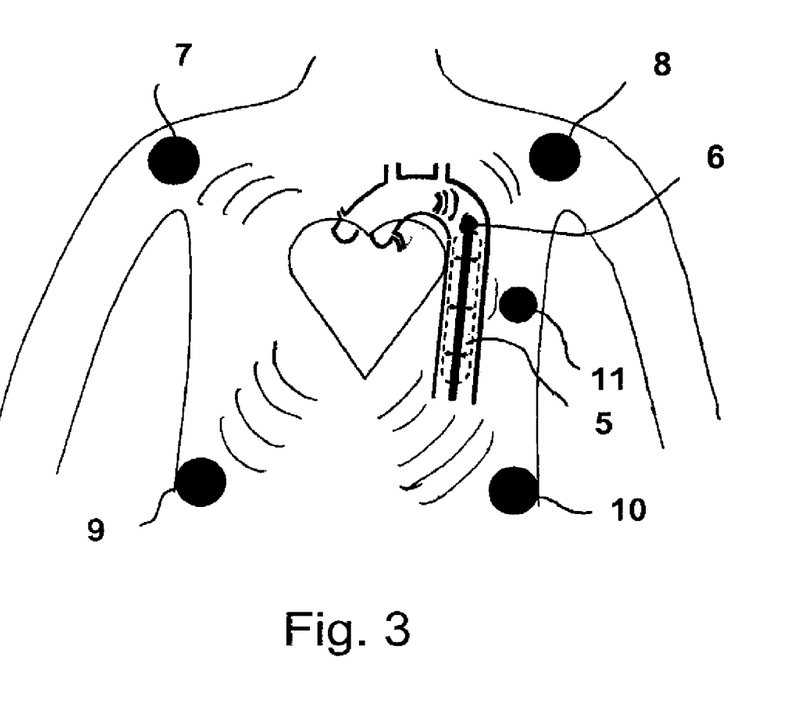
FIG. 3 is a schematic view of the upper body of a patient with electrodes for recording ECG signals and an intra-aortic balloon pump comprising a main sensor.

In this connection, as is shown in FIG. 3, the invention relates to a main sensor 6, which in the example shown is disposed at the tip of the balloon pump, however in any case is disposed in a fixed spatial relationship, for example at a fixed, known distance thereto or directly thereon, and which allows electrophysiological signals of the heart or of a fluid mechanics variable of the ejected blood flow to be detected. The main sensor is, for example, designed as an electrode or antenna, depending on the internal circuitry, or comprises such an element.

In addition, auxiliary sensor 7, 8, 9, 10, 11 are provided, which can be formed by electrodes for ECG measurement applied externally to the patient's body. Alternately, differently placed sensors are also conceivable, for example sensors which, as part of implanted devices, are not disposed on the body surface but in the body interior, but are suitable for recording electrophysiological cardiac signals. Such sensors can, for example, be provided in cardiac pacemakers or implanted defibrillators.

It is also conceivable to provide a lower number of auxiliary sensors, for example one, two, three or four auxiliary sensors, wherein a higher number allows a complex ECG vector to be attained, which allows more precise localization of the main sensor, and thus of the functional element 5, by comparison and linking to the signals from the main sensor 6.

Both the main sensor 6 and the auxiliary sensors record a respective temporal curve of the electrophysiological cardiac signals or other measured variables, so that the position of the main sensor can be determined by comparing and linking the signals from the main sensor to the signals of the remaining auxiliary sensors having various positions.

Figure 4:
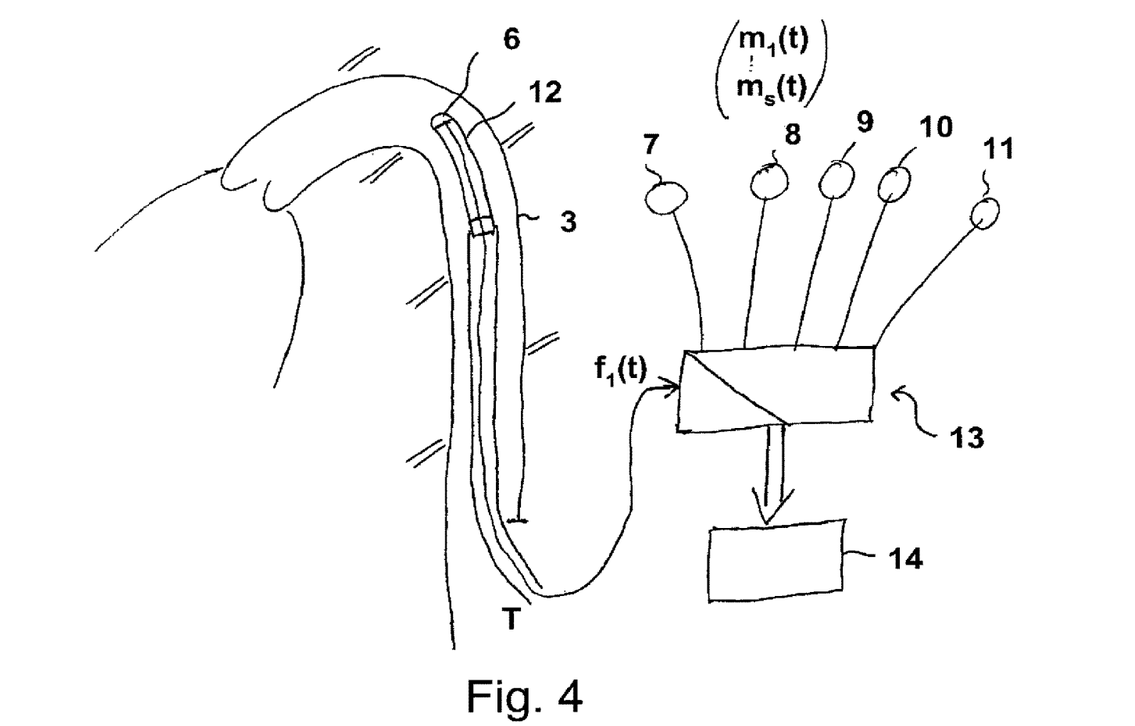
FIG. 4 is a schematic view of a blood vessel with a functional element, a main sensor and auxiliary sensors, and a processing unit.

In addition to the functional element 12, which can be a rotary pump, for example, the corresponding main sensor 6 at the tip of the functional element, and the auxiliary sensors 7, 8, 9, 10, 11, FIG. 4 shows a processing unit 13 in which the signals from all sensors are combined.

In the case of ECG data, the signals from the auxiliary sensors are combined to form a $$\begin{pmatrix} m_1(t) \\ \vdots \\ m_5(t) \end{pmatrix} \text{vector,}$$

while the temporally variable signal from the main sensor 6 is present as a scalar $f_1(t)$. The vector of the signals from the auxiliary sensors is compared to the function $f_1(t)$ so as to perform the position determination of the main sensor 6 in the processing unit 13 using predetermined metrics and to display the result in the display device 14. To this end, either the absolute distance of the functional element 12 from the inlet into the left ventricle, or the spacing along the blood vessel 3 can be shown in the display device.

Figure 5:
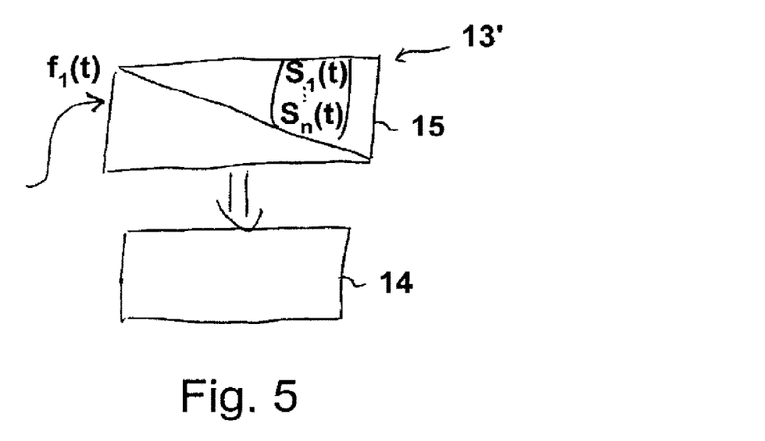
FIG. 5 is a schematic view of an alternative processing unit.

FIG. 5 shows an alternative embodiment of the processing unit, in which no $$\begin{pmatrix} s_1(t) \\ \vdots \\ s_n(t) \end{pmatrix}$$

currently detected electrophysiological signals are detected by auxiliary sensors and instead stored data is used. This data is stored in a memory unit 15 of the processing unit 13' and was, for example, measured when the treatment of the patient started and was archived, so as to later allow the position of the functional element to be determined by comparing the currently measured signals from the main sensor to typical signals of the patient's heart.

Figure 6:
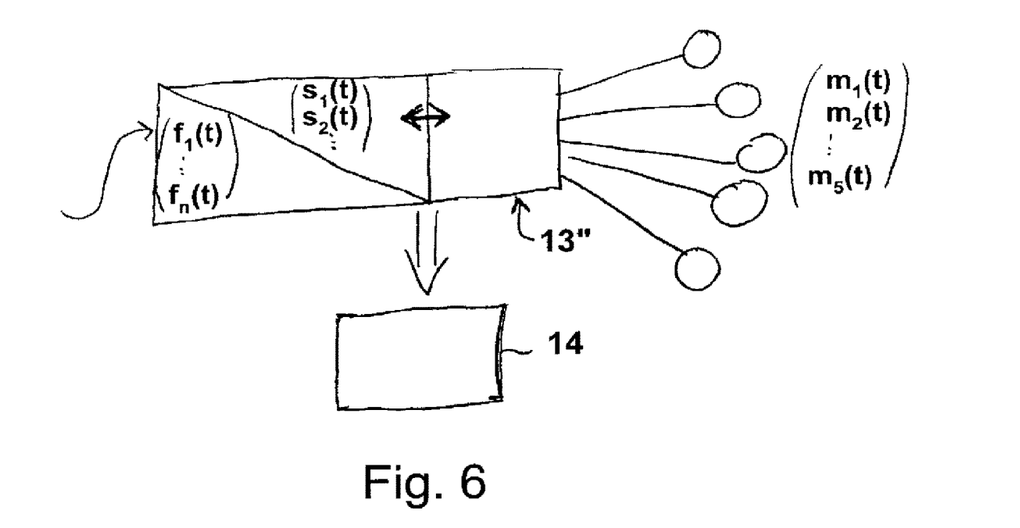
FIG. 6 is a further embodiment of a processing unit.

FIG. 6 shows a variant of the invention in which both currently measured electrophysiological heart signals $$\begin{pmatrix} m_1(t) \\ \vdots \\ m_5(t) \end{pmatrix}$$

and stored ECG data $$\begin{pmatrix} s_1(t) \\ \vdots \\ s_n(t) \end{pmatrix}$$

are linked to the signals from a main sensor. To this end, as in the example described based on FIG. 4, the signals from the main sensor can be $$\begin{pmatrix} f_1(t) \\ \vdots \\ f_n(t) \end{pmatrix}$$

recorded via several main sensor elements which are spatially distributed on the functional element 5, so that the main sensor also allows a signal vector to be detected. It is then possible to first compare the currently detected electrophysiological heart signals $$\begin{pmatrix} m_1(t) \\ \vdots \\ m_5(t) \end{pmatrix}$$

to the stored data $$\begin{pmatrix} s_1(t) \\ \vdots \\ s_n(t) \end{pmatrix}$$

and link the result of this comparison to the data detected by the main sensor, so as to output position information in the display unit 14 using metrics. To this end, either an absolute distance or a traffic light-type indicator in form of a green light for an allowed distance range, a yellow light for a critical distance range and a red light for a prohibited distance range of the functional element from the ventricle may be provided. As an alternative or in addition, the position may also be graphically represented, for example by a representation relative to the position of the heart or of a reference point, for example of an auxiliary sensor, the position of which can in particular be exactly known. Moreover, the position can also be represented by means of an acoustic signal, for example an alarm signal, which indicates the departure from the intended position or a change in distance from a predetermined location.

Figure 7:
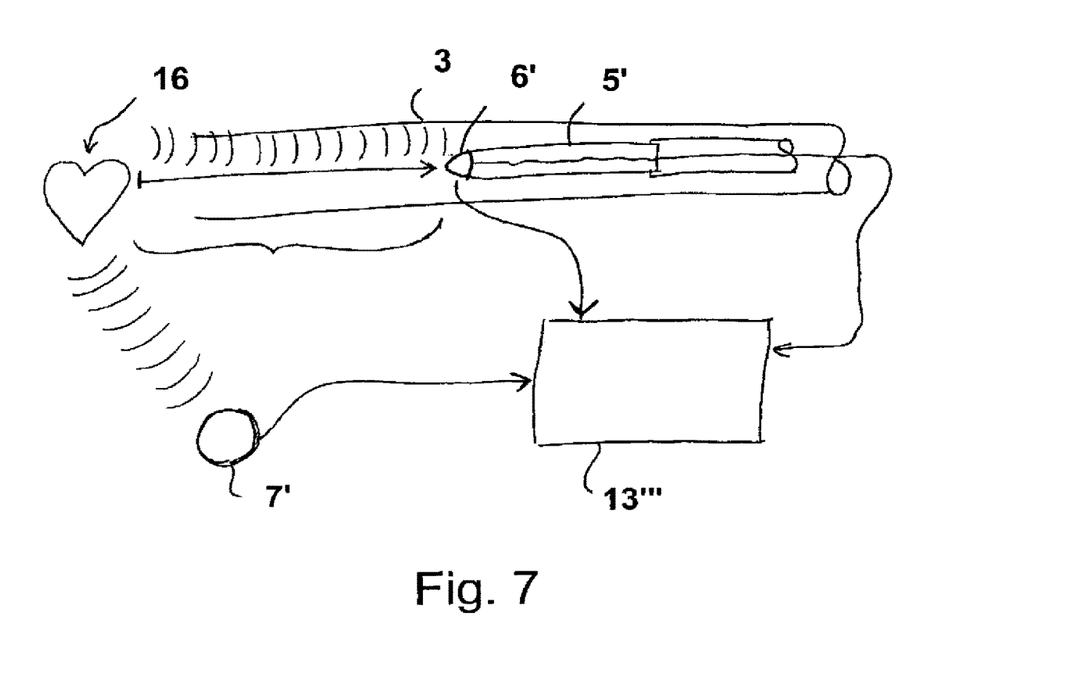
FIG. 7 shows an alternative embodiment of the medical product according to the invention, comprising a pressure sensor which forms the main sensor.

FIG. 7 shows an alternative design of a medical product according to the invention, in which a heart, which is shown symbolically and denoted by numeral 16, simultaneously emits electrophysiological signals which are recorded by means of one or more auxiliary sensors 7', and blood pressure fluctuations are transported via the vascular system due to the periodic pump activity, wherein the fluctuations can be recorded by means of a pressure sensor 6' at the tip of a functional element 5', for example a heart pump.

Because the electrophysiological signals are recorded by the sensors 7' virtually without delay, these convey a current picture of the cardiac activity, which can be compared to the pressure fluctuations arriving at the main sensor 6' with delay due to the slower migration velocity. It can be determined, or it is known, at what times with regard to a complete cardiac period certain maximal or minimal blood pressure values are generated in the heart, so that, having knowledge of the migration velocity of pressure waves, the distance of the main sensor 6' from the ventricle can be concluded from the time difference of the recording by the sensors 6', 7'. Using the configuration shown and a corresponding processing unit 13''', it is thus possible to determine the position of the main sensor 6', and thus that of the functional element 5', relative to the vascular system in relation to the heart and the position can be displayed.

The measurement is typically carried out based on the pressure maximum that is achieved. The measurement by means of the processing unit 13''' can be calibrated when introducing the functional element 5', for example by slowly inserting the blood vessel while also determining the position of the functional element 5' by means of imaging.

Figure 8:
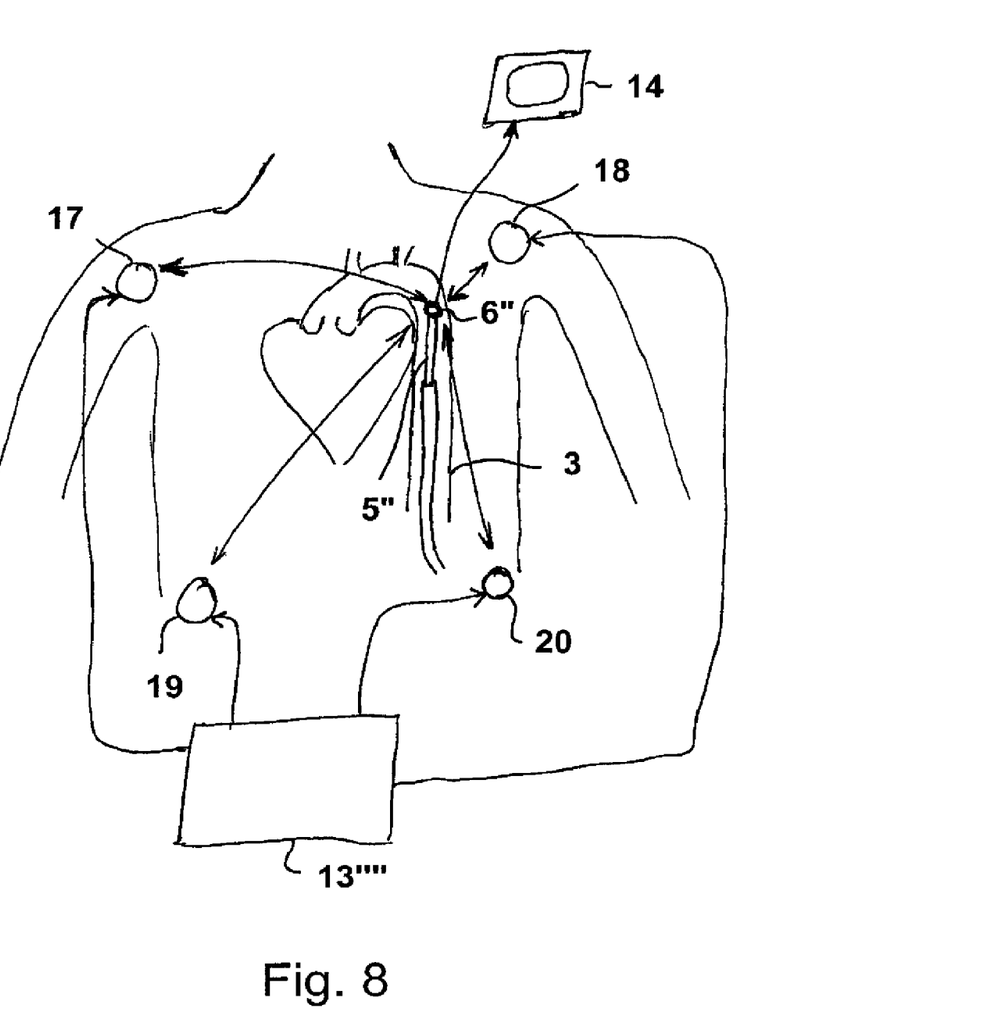
FIG. 8 shows a further alternative embodiment of the invention for determining the position of a functional element.

FIG. 8 shows a further alternative of the medical product according to the invention, in which a main sensor 6", which is disposed at the tip of a functional element 5''', interacts with several, notably two, three or four, auxiliary sensors or transceivers 17, 18, 19, 20, for example via magnetic fields, electrical fields or electromagnetic coupling. A corresponding transceiver may also be used as the main sensor 6", so that it either transmits signals received from the elements 17, 18, 19, 20, or vice versa. The intensity of the coupling of the elements 17, 18, 19, 20 to the respective element 6" can be used to determine the position thereof relative to the elements 17, 18, 19, 20. For example electrodes, which are already present and which are alternately used for position determination and as ECG electrodes, may be used as transceiver elements 17, 18, 19, 20.

The various coupling intensities are linked in the processing unit 13''''. In this case, it is also possible for several sensor elements to be disposed on the main sensor, for example so as to render the position determination more precise or additionally allow the orientation of the functional element to be determined.

Figure 9:
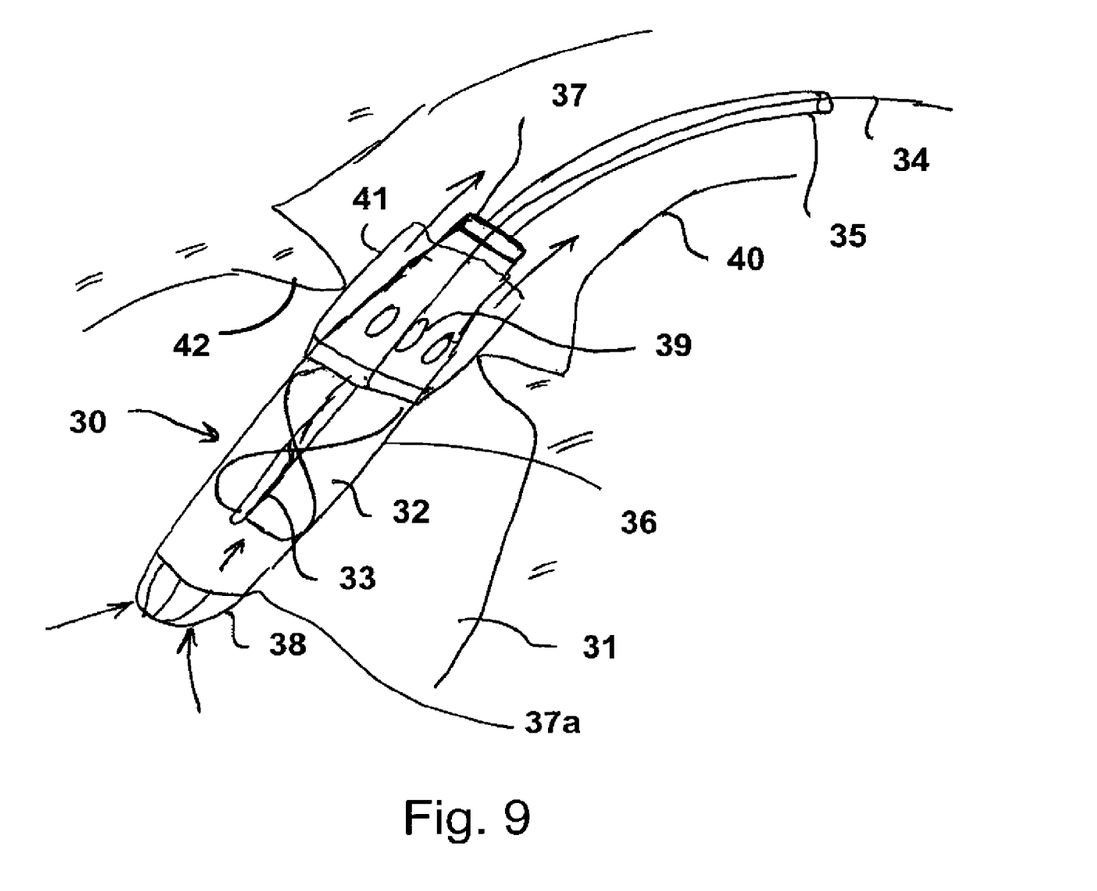
FIG. 9 shows an implantable heart pump comprising a rotor as an example of a functional element.

FIG. 9 shows a rotary pump 30 as the functional element by way of example, which is designed to be compressible and expandable for insertion in a ventricle 31. The pump 30 comprises a rotor 32 having a hub 33, which can be driven by means of a drive shaft 34 from outside the patient body. The drive shaft is guided through a hollow catheter 35, which is shown only partially. The pump 30 comprises a compressible pump housing 36, to the proximal end of which a main sensor 37 is attached. The main sensor can be connected to a processing unit disposed outside the body, for example via an electrical conductor located in the lumen or the housing wall of the hollow catheter 35, and notably via the drive shaft.

During operation, the pump takes in blood via the intake cage 38 and ejects the same into the blood vessel 40 via ejection openings 39. A flexible outflow hose 41 is provided, which in cooperation with the heart valve 42, which surrounds the outflow hose, periodically closes the ejection/outflow openings 39 and thus prevents the backflow of blood.

This demonstrates that the position of the pump relative to the heart valve must be precisely adhered to.

If the position of the main sensor 37 can be determined, it is also possible to correctly position the pump 30 in the ventricle.

In a modification, a further sensor 37a is attached to the distal end of the pump housing. In this case, it is possible to determine a corresponding signal, for example an ECG vector, directly between these two sensors and to draw a conclusion therefrom as to the position, or change in position, of the pump. Depending on the accuracy requirements in terms of the position determination, it may be possible in this instance to forego additional, notably external, auxiliary sensors.

An operating property of the blood pump may also be used to implement a main sensor which measures a fluid mechanics variable, for example the blood pressure or the flow velocity of the blood, for example in the case of a rotary pump the current rotational speed can be used if the driving power/torque is known, or a driving torque, driving power, or current/voltage/electrical power of a driving motor of the pump.

The current rotational speed and the electrical power required for driving purposes, which can be determined based on the drive current required by the driving motor, can be used to determine the flow velocity of the blood flow flowing through the pump in a time-resolved manner. When the heart is beating, this results in a periodic pattern, the phase angle of which can be compared to ECG data so as to determine the delay of the fluid mechanics changes from the heart to the main sensor, and thus the distance of the main sensor from the heart.

It is also possible to position two sensors in the same blood vessel, and using travel time measurements which are determined based on the measurement of fluid mechanics variables by each of the sensors, it is possible to determine the distance or a change in the distance of the two sensors. If the position of one of the sensors is fixed and/or known, it is also possible to determine and monitor the absolute position of the other sensor.

Figure 10:
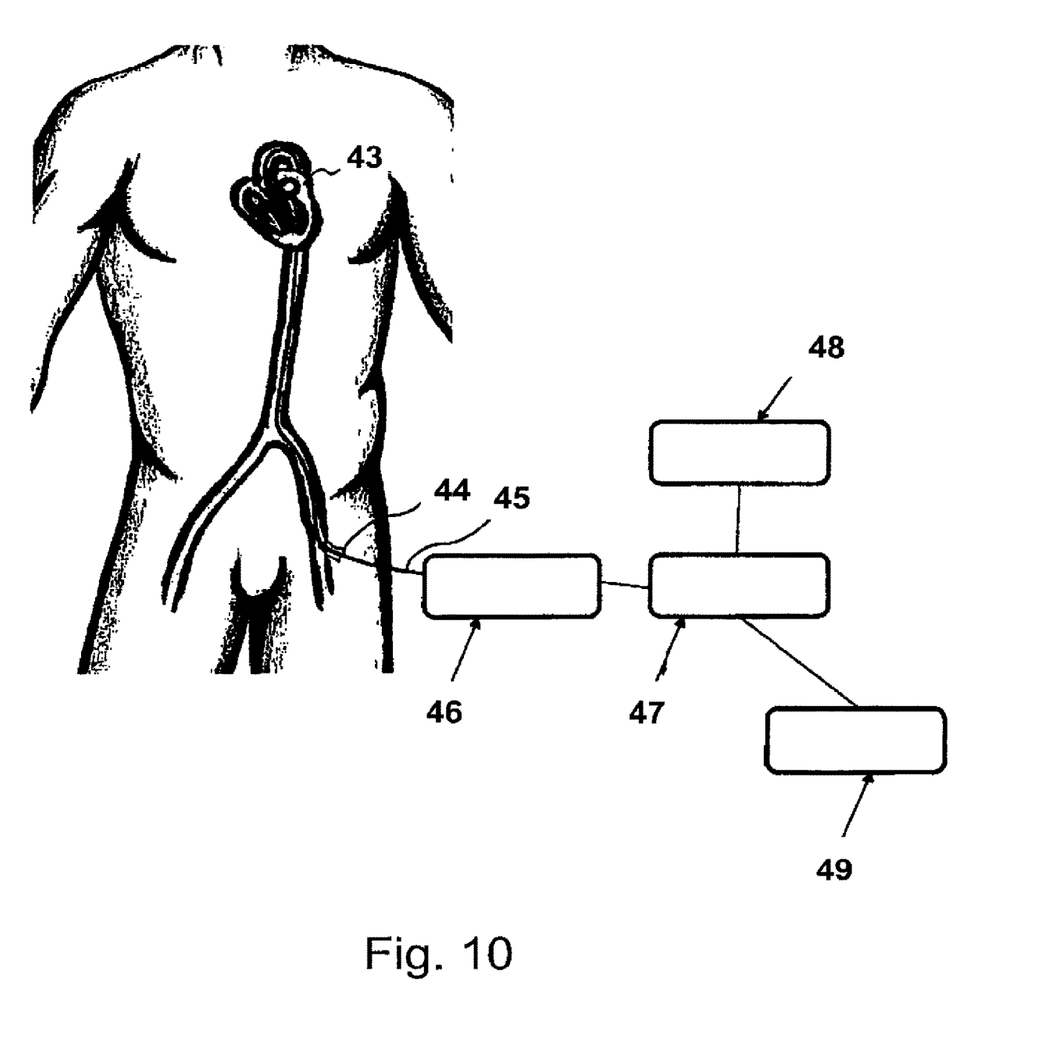
FIG. 10 shows a medical product comprising a blood pump and a processing unit for position monitoring and an alarm system.

FIG. 10 shows a patient body, the heart 43 of whom is supported by means of a blood pump which is placed in the heart valve by means of a catheter 44. A sensor is disposed on the blood pump, and the signals of the sensor are transported by means of a line 45 extending along the catheter 44, notably in the catheter. The signal detection takes place in a signal detection unit 46, which as an alternative or in addition can also receive radio signals and signals from sensors in the outside region of the patient, for example from ECG electrodes. The signal monitoring unit 47 monitors trends of the monitored signals and/or a comparison to reference signals for variances from threshold values and/or instances in which the same are exceeded. If a significant change or variance in the position is found, a signal is emitted to the alarm system 48, which communicates with the outside and optionally can initiate an adjustment of the position of the blood pump. During adjustment, the elimination of the alarm signal may serve as an indication that the desired position has been reached. The processing unit can also comprise a calibration system 49 for detecting and storing reference data when the desirable positioning is carried with methods other than those that are desirable.

The medical product described in this patent application can be used for visualizing the signals of the main sensor 6, 6', 6" for optimal positioning during the implantation process, enabling easier and safer placement of the medical product in the circulation. The visualization may take place on a screen of a user's console which is configured to show the position of the medical product within the human or animal body. The screen may be a touch screen configured to display and control the medical product during use. The visualization is very advantageous with regard to control of the medical product's position in the blood circuit. For instance, the position of a rotary blood pump in relation to a heart valve (see, for example, FIG. 9 of the instant patent application) can be easily controlled by medical personnel, and any necessary corrections can be made by repositioning the medical product according to the vectors displayed on the above-mentioned screen.

The invention claimed is:

1. A method of determining a position of a blood pump in a body of a patient, the method comprising:
    inserting a blood pump into a heart of a patient, the blood pump having a housing, wherein the housing surrounds a rotor;
    actuating the rotor;
    receiving, at a processing unit, a first signal, wherein the first signal represents a rotational speed of the rotor;
    determining, at the processing unit, based on the first signal, a flow velocity of a periodic blood flow through the blood pump;
    determining, at the processing unit, a phase angle of the periodic blood flow;
    detecting, at a main sensor having a constant position relative to the blood pump, a second signal, wherein the second signal is indicative of a cardiac parameter; and
    determining, from the phase angle of the periodic blood flow and the second signal, the position of the blood pump within the body of the patient.

2. The method of claim 1, further comprising detecting, with the processing unit, a change in the position of the blood pump.

3. The method of claim 2, further comprising generating a third signal when a threshold for the change is exceeded.

4. The method of claim 1, further comprising storing, in a memory unit connected to the processing unit, at least one previously determined position of the blood pump.

5. The method of claim 4, further comprising continuously comparing a currently determined position of the blood pump to the at least one previously determined position of the blood pump stored in the memory unit.

6. The method of claim 5, further comprising determining a difference between the at least one previously determined position of the blood pump and the currently determined position of the blood pump.

7. The method of claim 6, further comprising generating a fourth signal if the difference exceeds an established threshold.

8. The method of claim 1, further comprising monitoring, with the processing unit, the position of the blood pump based on a distance between the main sensor and the blood pump and a position of the main sensor within the body of the patient.

9. The method of claim 1, wherein the second signal is an electrophysiological heart signal.

10. The method of claim 9, further comprising comparing the phase angle of the periodic blood flow to the electrophysiological heart signal.

11. The method of claim 1, wherein the rotational speed of the rotor is determined based on a drive current or a power supplied to the rotor.

12. A blood pump system comprising:
    a blood pump;
    a pump housing surrounding a pump rotor, the pump rotor configured to be actuated;
    a main sensor having a constant position relative to the pump housing; and
    a processing unit configured to:
        receive a first signal, wherein the first signal represents a drive current or a power supplied to the pump rotor;
        receive a second signal, wherein the second signal is indicative of a cardiac parameter;
        determine from the first signal a phase angle of a periodic blood flow through the pump housing; and
        compare the phase angle of the periodic blood flow to the second signal to determine a position of the blood pump within a body of a patient.

13. The blood pump system of claim 12, wherein the processing unit is further configured to detect a change in the position of the blood pump.

14. The blood pump system of claim 13, wherein the processing unit is configured to generate a third signal when a threshold for the change is exceeded.

15. The blood pump system of claim 12, further comprising a memory unit connected to the processing unit, wherein the memory unit is configured to store at least one previously determined position of the blood pump.

16. The blood pump system of claim 15, wherein the processing unit is further configured to continuously compare a currently determined position of the blood pump to the at least one previously determined position of the blood pump stored in the memory unit.

17. The blood pump system of claim 16, wherein the processing unit is further configured to determine a difference between the at least one previously determined position of the blood pump and the currently determined position of the blood pump.

18. The blood pump system of claim 17, wherein the processing unit is configured to generate a fourth signal if the difference exceeds an established threshold.

19. The blood pump system of claim 12, wherein the processing unit is further configured to monitor the position of the blood pump based on a distance between the main sensor and the pump housing and a position of the main sensor within the body of the patient.

20. The blood pump system of claim 19, wherein the main sensor is disposed on the pump housing.

21. The blood pump system of claim 20, wherein the main sensor is disposed on a proximal end of the pump housing.

22. The blood pump system of claim 12, wherein the processing unit further comprises a calibration system for detecting and storing reference data.

23. The blood pump system of claim 12, wherein the first signal represents the power supplied to the pump rotor.

24. The blood pump system of claim 12, wherein the second signal is an electrophysiological heart signal.

* * * * *